United States Patent [19]

Meek, deceased et al.

[11] Patent Number: Plant 5,661

[45] Date of Patent: Feb. 11, 1986

[54] CHRYSANTHEMUM PLANT NAMED GOLDMINE

[75] Inventors: Jack M. Meek, deceased, late of Salinas, Calif.; by Saundra J. Meek, executrix, Canyon, Tex.; William E. Duffett, Salinas, Calif.; Grace H. Mack, 108 Wahackme Rd., New Canaan, Conn. 06840

[73] Assignee: Grace H. Mack, New Canaan, Conn.

[21] Appl. No.: 514,194

[22] Filed: Jul. 15, 1983

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar named Goldmine having round pompon capitulum form, formal decorative capitulum type, dark yellow ray floret color, diameter across face of capitulum up to 45 mm., short plant height, spreading branching pattern, average natural season flowering date of September 15, and average flowering response period of seven (7) weeks in photoperiodic controlled short day programs.

3 Drawing Figures

The present invention comprises a new and distinct cultivar of *Chrysanthemum morifolium,* Ramat., hereinafter referred to by the cultivar name Goldmine.

Goldmine is a product of a planned breeding program which had the objective of creating cultivars with decorative capitulum type, short height, spreading branching pattern, durable inflorescence, seven (7) week flowering response period, and yellow ray floret color under outdoor natural season conditions.

Goldmine was originated from a cross made by Grace H. Mack in a controlled breeding program in New Canaan, Conn. in the year 1978. The female parent was Y2249, a yellow decorative, an unnamed seedling selected from a cross of 4877×Patriot (disclosed in U.S. Plant Pat. No. 3,897). The male parent was Y2132, a yellow decorative of pompon form, an unnamed seedling derived from a cross of M544×Minnyellow.

Goldmine was discovered and selected as a flowering plant within the progeny of the stated cross by J. Michael Meek on Sept. 14, 1979 in an outdoor field in Salinas, Calif.

The first act of asexual reproduction of Goldmine was accomplished when vegetative cuttings were taken from the initial selection in 1980 in Salinas, Calif. by William E. Duffett. Horticultural examination of selected units initiated in 1981 has demonstrated that the combination of characteristics as herein disclosed for Goldmine are firmly fixed and are retained through successive generations of asexual reproduction.

Goldmine has not been observed under all possible environmental conditions. The phenotype may vary significantly with variations in environment such as temperature, light intensity, and day length. The following observations, measurements, and comparisons describe plants grown in a field in Salinas, Calif.

Rooted cuttings were established in soil in one gallon containers maintained outdoors under the natural temperature and day length prevailing during July through September. Single pinching was practiced with all branches and buds retained.

The following traits have been repeatedly observed and are determined to be basic characteristics of Goldmine which in combination distinguish this chrysanthemum as a new and distinct cultivar:

(1) Round pompon capitulum form.

(2) Formal decorative capitulum type.

(3) Dark yellow ray floret color.

(4) Diameter across face of capitulum up to 45 mm.

(5) Short plant height.

(6) Spreading branching pattern.

(7) Average natural season flowering date of September 15.

(8) Average flowering response period of seven (7) weeks in photoperiodic controlled flowering programs.

The accompanying photographic drawings show typical inflorescence and foliage characteristics of Goldmine. Sheet 1 is a color photograph of Goldmine. Sheet 2 is a black and white photograph showing three views of the inflorescence of Goldmine. Sheet 3 is a black and white photograph showing the leaves of Goldmine at three stages of growth (mature, intermediate, immature).

Of the many commercially available cultivars known to the present inventors, the most similar existing cultivar in comparison to Goldmine is the yellow cultivar Westpoint, disclosed in U.S. Plant Pat. No. 4,517.

Reference is made to attached Chart A which compares certain characteristics of Goldmine with the same characteristics of Westpoint. It will be noted that in comparison to Westpoint, Goldmine has darker ray floret color, earlier average natural season flower date, and larger diameter across the face of capitulum. The capitulum form, capitulum type, plant height, branching pattern, and plant spread of Goldmine are similar to those characteristics of Westpoint.

In the following description, color references are made to The Royal Horticultural Society Colour Chart. The color values were determined between 2:30 and 3:00 P.M. on Sept. 15, 1981 under 150 foot-candle light intensity at Salinas, Caif.

Botanical classification: *Chrysanthemum morifolium,* Ramat., cv Goldmine.

I. Inflorescence:

A. *Capitulum.*—Form: Round, pompon. Type: Formal decorative. Permanence: 3 to 4 weeks. Diameter across face: 35 to 45 mm.

B. *Corolla of ray florets.*—Color (abaxial): Approximately 13A oxidizing to 12A. Color (adaxial): Approximately 12A oxidizing to 12B.

C. *Reproductive organs.*—Androecium: present disc florets. Gynoecium: present both ray and disc florets.

D. *Disc florets.*—Color: Approximately 14A.

II Plant:

A. *General appearance.*—Spreading branching pattern; short height.

B. *Foliage.*—Foliage (abaxial): 137A. Foliage (adaxial): 137C.

CHART A
COMPARISON OF GOLDMINE AND WESTPOINT

| CULTIVAR | RAY FLORET COLOR | CAPITULUM FORM AND TYPE | AVERAGE NATURAL SEASON FLOWER DATE |
|---|---|---|---|
| GOLDMINE | DARK YELLOW | ROUND POMPON FORMAL DECORATIVE | SEPTEMBER 15 |
| WESTPOINT | MEDIUM YELLOW | ROUND POMPON FOR- | SEPTEMBER 25 |

-continued

CHART A
COMPARISON OF GOLDMINE AND WESTPOINT

| CULTIVAR | PLANT HEIGHT | BRANCHING PATTERN AND SPREAD | DIAMETER ACROSS FACE OF CAPITULUM |
|---|---|---|---|
| | | MAL DECORATIVE | |
| GOLDMINE | SHORT | SPREADING | 35 to 45 mm. |
| WESTPOINT | SHORT | SPREADING | 25 to 40 mm. |

COMPARISONS MADE OF PLANTS GROWN UNDER NATURAL SEASON OUTDOOR FIELD CONDITIONS IN SALINAS, CALIFORNIA

We claim:

1. A new and distinct cultivar of *Chrysanthemum morifolium,* Ramat., plant known by the name Goldmine, as described and illustrated, and particularly characterized as to uniqueness by the combined characteristics of round pompon capitulum form, formal decorative capitulum type, durable inflorescence, dark yellow ray floret color, diameter across face of capitulum up to 45 mm., short plant height, spreading branching pattern, average natural season flowering date of September 15, and average flowering response period of seven (7) weeks in photoperiodic controlled short day programs.

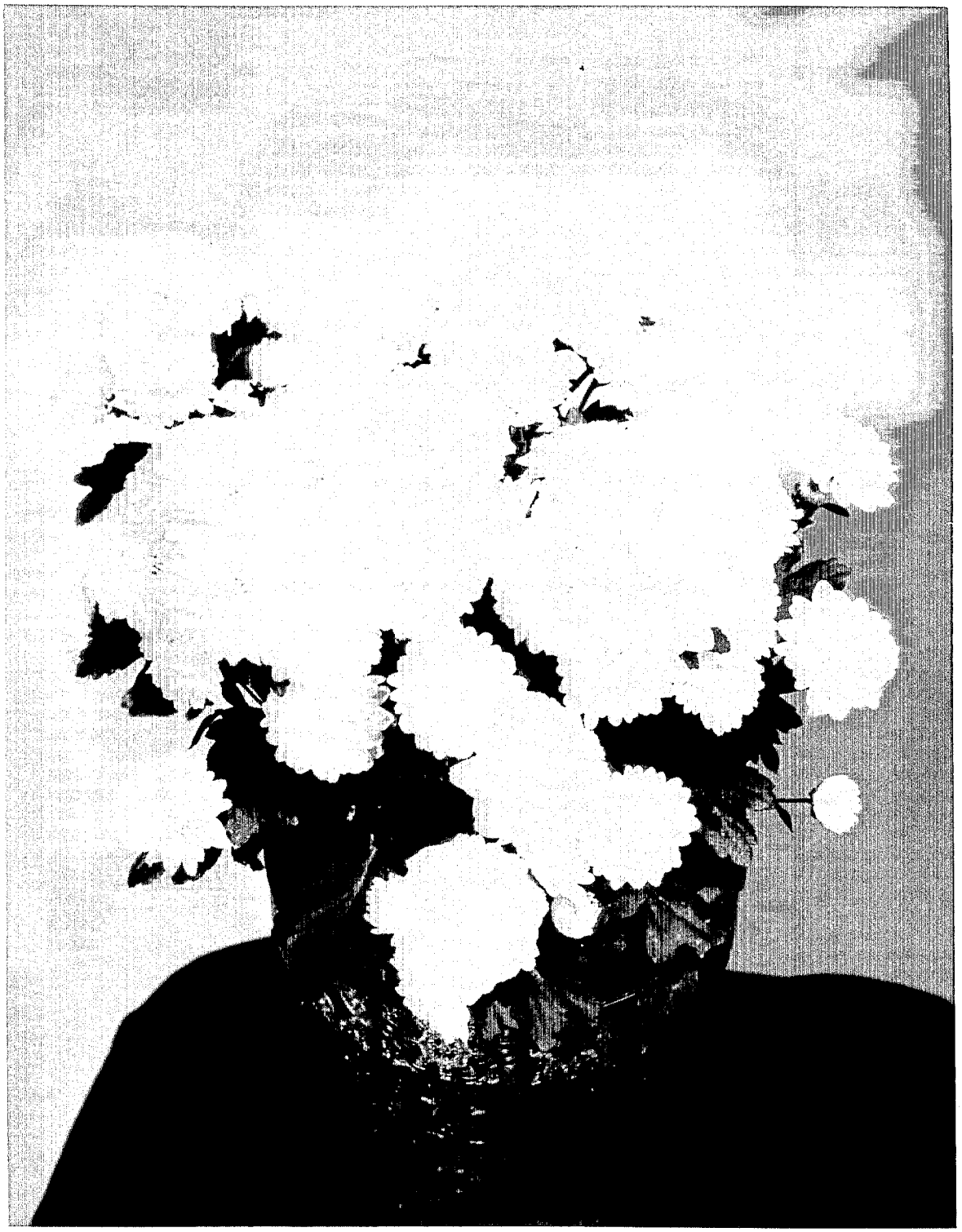

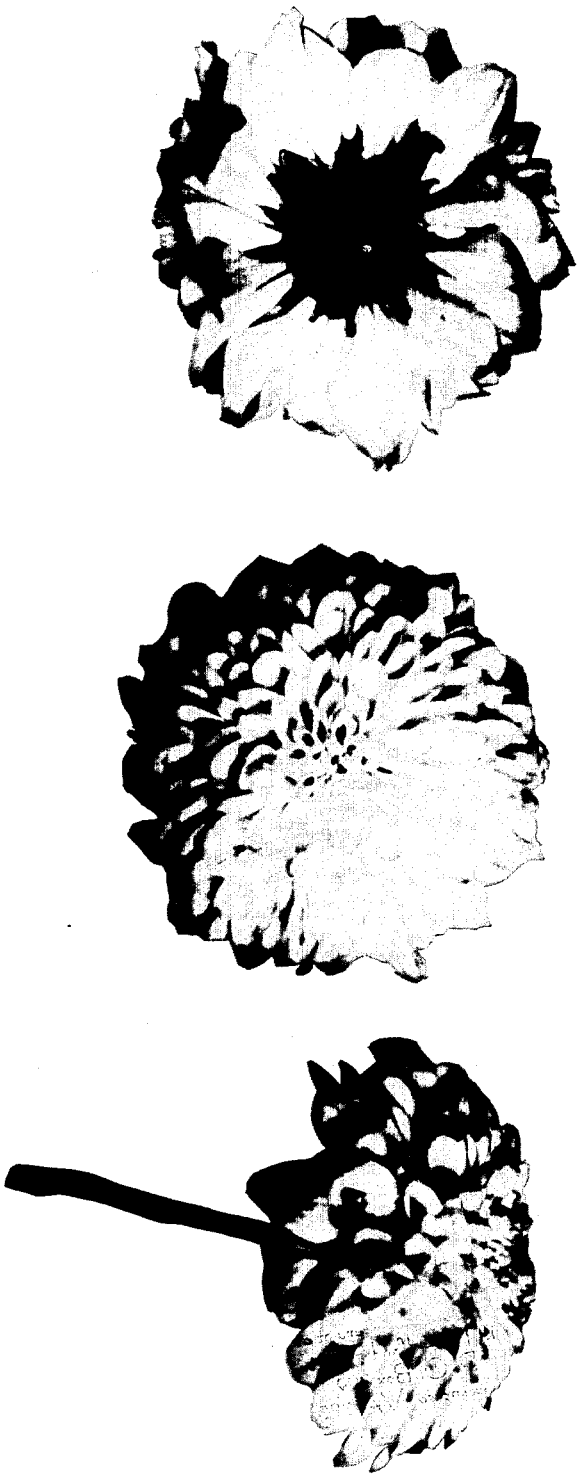

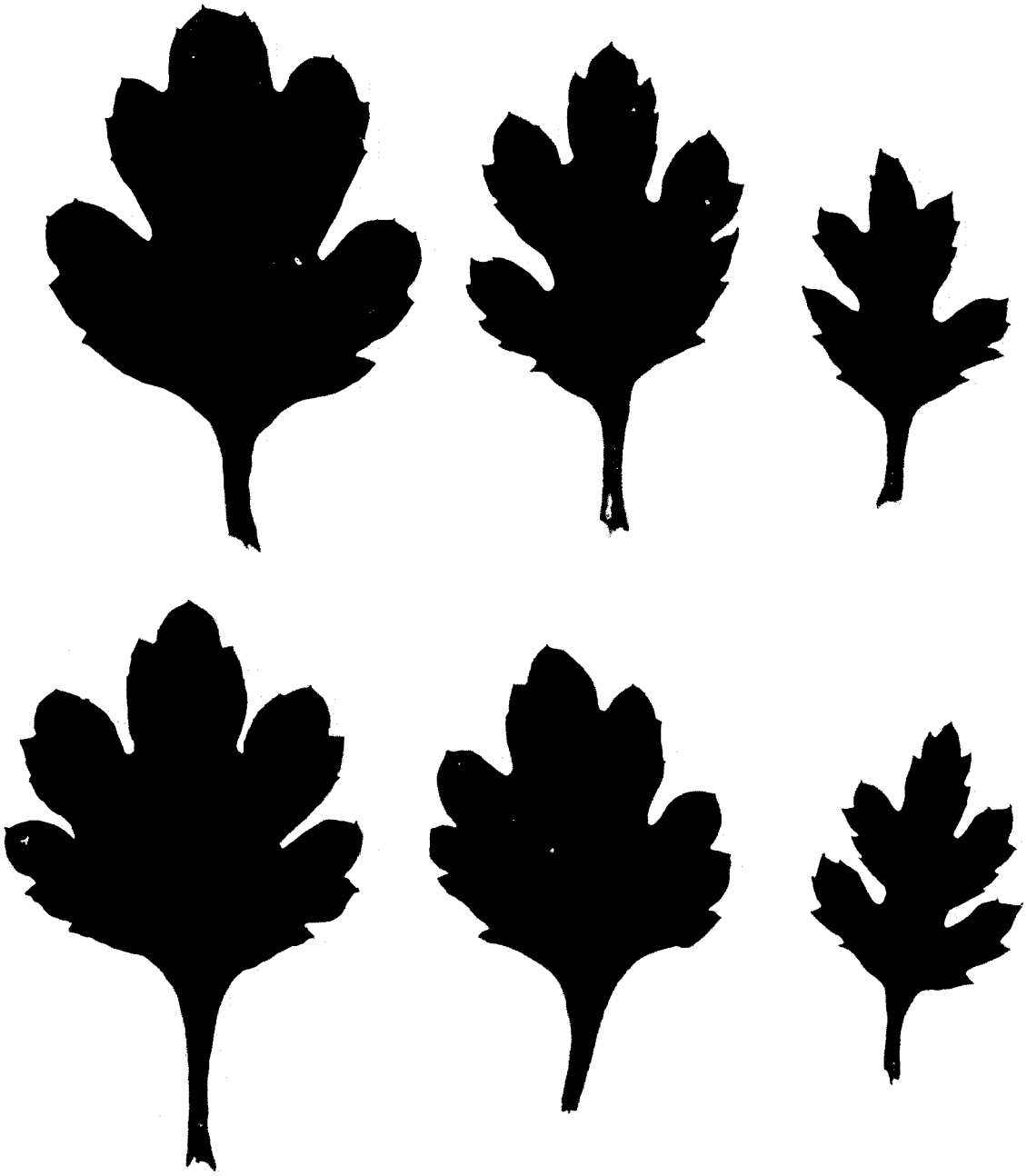

* * * * *